United States Patent [19]

Murakami et al.

[11] Patent Number: 5,137,824
[45] Date of Patent: Aug. 11, 1992

[54] CSF-1 GENE PROMOTER

[75] Inventors: Koji Murakami; Hiroshi Nakakubo; Teruo Kaneda, all of Osaka; Masanori Nagai, Kyoto; Hirofumi Arimura, Osaka, all of Japan

[73] Assignee: The Green Cross Corporation, Osaka, Japan

[21] Appl. No.: 168,016

[22] Filed: Mar. 14, 1988

[30] Foreign Application Priority Data

Mar. 13, 1987 [JP] Japan .................. 63-56890

[51] Int. Cl.⁵ ............ C12P 21/02; C12P 15/34; C12N 15/00; C12N 7/00; C12N 5/00; C07H 15/12
[52] U.S. Cl. ............. 435/240.2; 435/69.1; 435/91; 435/172.3; 435/235.1; 435/320.1; 536/27; 935/27; 935/32; 935/34; 935/56; 935/57; 935/70
[58] Field of Search ........ 435/69.1, 91, 172.3, 435/235, 240.2, 320, 19, 32, 41, 58, 61, 70, 81; 536/27; 530/350

[56] References Cited

U.S. PATENT DOCUMENTS 4,349,629  9/1982  Carey et al. .................... 435/68
4,663,283  5/1987  Kleid et al. .................... 435/91

OTHER PUBLICATIONS

Pouwels et al Cloning Vectors, A Laboratory Manual Elsevier pp. VIII-1-VIII-7 (1985).
Old et al Principles of Gene Manipulation, Studies in Microbiology vol. 2 pp. 104-109 & 275-278 (1985).
Palmiter et al Science vol 222 pp. 809-814 (1983).
Kawasaki, E. et al Science vol. 230 pp. 291-296 (1985).
Maniatis, T. et al Molecular Cloning, A Laboratory Manual Cold Spring Harbor Laboratory, CSH NY (1982) pp. 404-433.
Maxam et al, Methods in Enzymology vol 65 pp. 499-561 (1980).
Ladner, M. et al EMBO, J. vol. 6 pp. 2693-2698 (1987).

Primary Examiner—Joan Ellis
Attorney, Agent, or Firm—Sughrue, Mion, Zinn, Macpeak & Seas

[57] ABSTRACT

A CSF-1 gene promoter region is disclosed. This nucleotide base sequence is useful as a promoter for gene expression in animal cells.

4 Claims, 6 Drawing Sheets

```
-1311  -1301       -1291       -1281       -1271       -1261       -1251       -1241
AGTACT GTGGAGAATG  AATGGATGGC  AAATGACTTA  TCAGAGCCAG  CATTGAGGAA  TGAGCCAAGT  CCAATGGAA
ScaI

-1231       -1221       -1211       -1201       -1191       -1181       -1171       -1161
CACAGGAAAA  GGACCCTTTG  CTCTGCCAGG  AGAGTCACAG  AAGGCTTTGC  TGGTGGAGGA  TGAGATGCAA  TTTCACCTGA

-1151       -1141       -1131       -1121       -1111       -1101       -1091       -1081
AATGATGAGG  AGTTTGTCTT  CACCATGTGG  AGAAAGGAGC  ATTCAGGCAG  AGGGACCAGT  CTGAGCAAAG  GCATTCGGGT

-1071       -1061       -1051       -1041       -1031       -1021       -1011       -1001
GTAAAATTAT  TGCCTAGGAT  TGGAGTGAAG  GATATGTAGC  GCTACTGACA  AGAGACTCCT  CTTCAAGAGC  AGGCCACATA

-991        -981        -971        -961        -951        -941        -931        -921
TCCTTTATTT  CCCAGGGGTG  GAAACGGGCA  ACCTCACAGA  GGAATTGAAT  CATAATGAAT  TGAAGAAAGA  AAAATCTCCT

-911        -901        -891        -881        -871        -861        -851        -841
GAAGTTGGCA  TTATAATTAA  TAGGCTTAGG  CTCATCCTAC  TAGTCCTCAC  TTAGACTCAT  TCTCATGTAG  AAACAAAACG

-831        -821        -811        -801        -791        -781        -771        -761
TGATTAATCA  CCTCAGTAAG  TGCAATTTCC  AAAAACATCC  AGGGAAATCT  AGGGTCCAGG  TGCAGGACCT  TTCCAATCTG

-751        -741        -731        -721        -711        -701        -691        -681
AGTTGGATTT  TGCCTCCAGG  AGAGAGCATG  G TACCAGCC  AGCATTTCA   TCATCTAAGG  GTCAGGTGCC  TTGAAGTGTC
                              KpnI

-671        -661        -651        -641        -631        -621        -611        -601
TGCTGGCACC  CAGGGAAGAG  CCCCCCAGCT  TGCTGTCACA  GGACACAGCT GCTCCCTTCC  TGGCCAGTTA  GCCTCGTGCC
                                               PvuII
                                   -551
                                   CTGCAGAGGA
                                   PstI

-591        -581        -571        -561        -551        -541        -531        -521
CTCCCAGAAT  GGACTTGAAG  CTGGCCGGGC  TGCTTGGGGG  CTGCAGAGGA  AGAAGGGGGC  TGCCGGCAAA  CCTGCTGACT
```

```
-511       -501       -491       -481       -471       -461       -451       -441
CAGGCTCCAC GAGGGACGAA GTAACACTGG ACTCCTTTCG GCACTCCGAG AATGGGGTGG GGGCGTCTTC AAAGGATTTC
-431       -421       -411       -401       -391       -381       -371       -361
CCTCCCTTCC CAGTGCTTGT CCCTGCTCTC GGTCCGTTTT CTGCTAAGAT TTGGGGATTT TCAGGCCTGG AGGAAAGTCC
-351       -341       -331       -321       -311       -301       -291       -281
CTTGGGACGA TCATAGAGCG CTAGCATGAA TCACCTGAGA GCGCGGAAGG AAAGGGTCGG TCCCAGAGGC GCGGGAAGG
-271       -261       -251       -241       -231       -221       -211       -201
CAGGGTGGGC GGACTAGGAG CCCGCGCTCG TTTGCTGAAG GCTTGGAAGT GCAGCCAGA  AGACAGAGGG TGACTAGGAA
-191       -181       -171       -161       -151       -141       -131       -121
GACGCCGAGC GGGGCTGCGC CCCGCGGGT  GGGGAGGGG  AGGCGGGGA  AGGCGGCTGA GTTGGGCCTC TGGATTGTGT
-111       -101       -91        -81        -71        -61        -51        -41
GTGTCTGTGT CAGTGTGTGT GTGTATGTGT GTGTTCGGCG CCTGGCCAGG CTGGCCAGG  GTGATTTCCC ATAAACCACA
-31        -21        -11        -1         10         20         30         40
TGCCCCCCAG TCCTCTCTTA AAAGCTGCCG AGGGCTGGCC AGTGAGGCTC GCCCGGGGA  AAGTGAAAGT TTGCCTGGGT
                                                        SmaI
50         60         70         80         90         100        110        120
CCTCTCGGGG CCAGAGCCGC TCTCCCGCATC CCAGGACAGC GGTGCGGCCC TCGGCCGGGG CGCCCACTCC GCAGCACCCA
130        140        150        160        170        180        190        200
GCGAGCGAGC GAGGGAGCGA GGGGCGGGCCGA CGCGCCCGGC CGGGACCCAG CTGCCCGTAT GACCGGCCCG GGGCGCCCG
                                               PvuII      |→Coding region
210        220        230
GGGCGCTGCCC TCCCACGGTA AGGCGACGGCC GCG
                  |→    Intron
```

CSF-1 GENE PROMOTER

FIELD OF THE INVENTION

This invention relates to a novel, CSF-1 gene promoter. This nucleotide base sequence is a promoter for use in animal cell gene expression systems.

BACKGROUND OF THE INVENTION

A promoter is a DNA signal for starting mRNA synthesis (transcription) with DNA as a template. The promoter has a role in determining the efficiency of transcription.

One of the first hosts used for the production of desired physiologically active substances by means of recombinant DNA technology was *Escherichia coli* as the host. Shortly thereafter, microorganisms such as *Saccharomyces cerevisiae* and *Bacillus subtilis* joined the class of hosts in frequent use because of the ease with which they can be cultured and of the advancement resulting from the study of host-vector systems. (cf. Goeddel, D. V., Itakura, K. et al., Proc. Natl. Acad. Sci. USA, 76, 106 (1979) and Nagata, S., Taira, S. H. and Weissmann, C., Nature, 284, 1316 (1980)).

Recently, to produce macromolecular glycoproteins in a form similar to their naturally occurring form and at the same time in a soluble form by means of recombinant DNA technology, interest has been drawn to expression systems in which animal cells are used as hosts.

The development of promoters for gene expression in animal cells, however, has been slow and, at present, only the SV40 promoter, metallothionein promoter and a few others are known.

CSF-1, one of many colony stimulating factors acts on and promotes the differentiation and proliferation of human macrophages.

In recent years, new information on the base sequence of cDNA coding for CSF-1 has been collected by using genetic engineering techniques (WO 86/04607; Kawasaki et al; Science, 230, 291-296 (1985), Ladner, et al., EMBO Journal, 6, 2693-2698 (1987) and Wong, et al., Science, 235, 1504-1508 (1987)).

Based on the above findings, the present inventors directed their attention to the CSF-1 gene in their attempt to develop a promoter for expression in animal cells.

As a result of intensive investigation in search of a novel promoter, the promoter region upstream from the 5' end of the human CSF-1 gene was analyzed and the results therefrom are presented herein.

SUMMARY OF THE INVENTION

The present invention thus provides a CSF-1 gene promoter region comprising the following nucleotide base sequence.

```
          -511         -501         -491         -481         -471
          CAGGCTCCAC   GAGGGACGAA   GTAACACTGG   ACTCCTTTCG   GCACTCCGAG

-461         -451         -441         -431         -421
          AATGGGGTGG   GGGCGTCTTC   AAAGGATTTC   CCTCCCTTCC   CAGTGCTTGT

-411         -401         -391         -381         -371
          CCCTGCTCTC   GGTCCGTTTT   CTGCTAAGAT   TTGGGGATTT   TCAGGCCTGG

-361         -351         -341         -331         -321
          AGGAAAGTCC   CTTGGGACGA   TCATAGAGCG   CTAGCATGAA   TCACCTGAGA

-311         -301         -291         -281         -271
          GCGCGGAAGG   AAAGGGTCGG   TCCCAGAGGC   GCGGGGAAGG   CAGGGTGGGC

-261         -251         -241         -231         -221
          GGACTAGGAG   CCCGCGCTCG   TTTGCTGAAG   GCTTGGAAGT   GCAGCGCAGA

-211         -201         -191         -181         -171
          AGACAGAGGG   TGACTAGGAA   GACGCCGAGC   GGGGCTGCGG   GCCGGCGGGT

-161         -151         -141         -131         -121
          GGGGGAGGGG   AGGCGGGGGA   AGGCGGCTGA   GTTGGGCCTC   TGGATTGTGT

-111         -101         -91          -81          -71
          GTGTCTGTGT   CAGTGTGTGT   GTGTGTGTGT   GTGTATGTGT   GTGTTCGGCG

-61          -51          -41          -31          -21
          CCTGGCCAGG   GTGATTTCCC   ATAAACCACA   TGCCCCCCAG   TCCTCTCTTA

-11          -1
          AAAGCTGCCG   AGGGCTGGCC
```

BRIEF DESCRIPTION OF THE DRAWINGS

FIG. 1A and FIG. 1B show shows the nucleotide base sequence of a region which is upstream from the CSF-1 gene and contains the CSF-1 gene promoter, wherein +1 is the 5' end of the cDNA reported by Kawasaki et al., — indicates a G-T cluster, ... indicates a region homologous to the enhancer-core region of the immunoglobulin heavy chain gene and = indicates a region homologous to the consensus sequence upstream from the lymphokine gene.

In FIG. 4A, ▨ indicates the nucleotide sequence determination region. FIG. 4B shows the restriction enzyme cleavage map expected from the nucleotide base sequence.

In FIG. 5, ■ indicates exon and ▨ indicates the nucleotide base sequence determination region upstream from the 5' end of Exon I according to the invention.

DETAILED DESCTIPTION OF THE INVENTION

Figure 2:
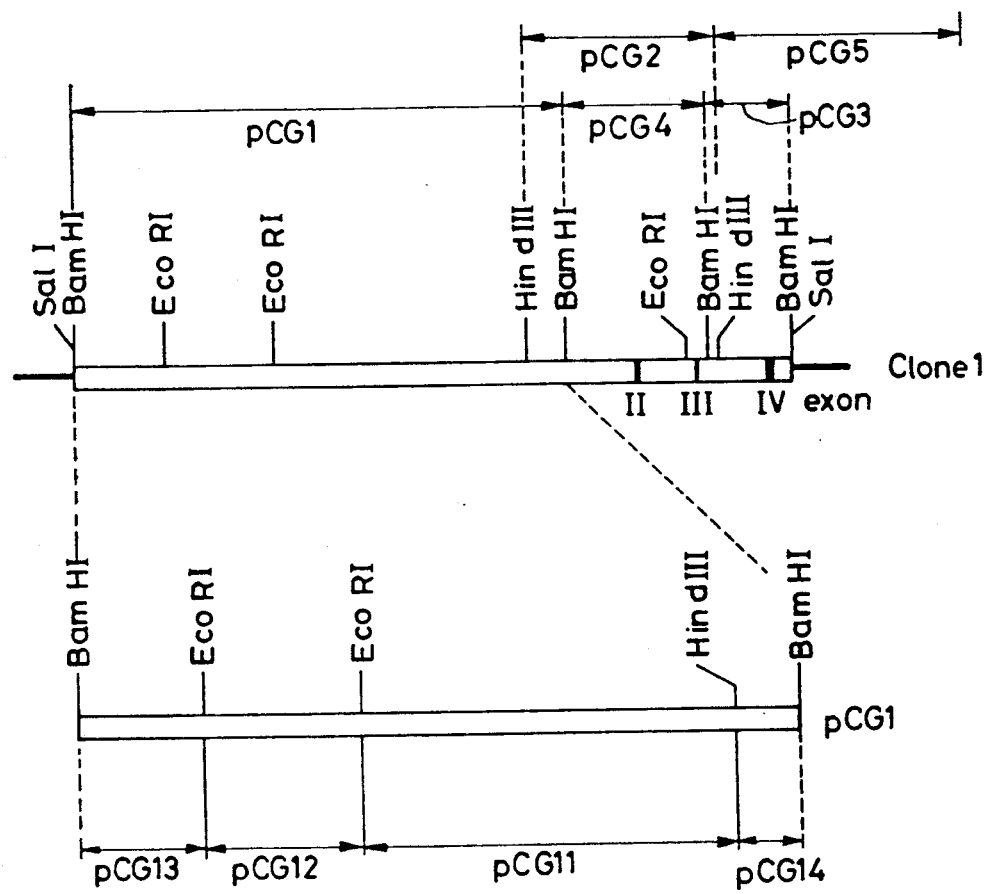
FIG. 2 shows the restriction enzyme map of clone 1 as well as the subcloning thereof.

As the starting material, cells for obtaining the promoter according to the invention, include human liver cells and human peripheral blood leukocytes, among others.

To obtain the promoter, human chromosomal DNA is extracted from such starting material cells as described in, e.g., Maniatis et al., "Molecular Cloning," Cold Spring Harbor Laboratory, N.Y. (1982), followed by partially digesting the DNA with an appropriate restriction enzyme, e.g., Sau3Al, HaeIII, AluI and BamHI. The fragments are introduced into an appropriate phage vector, e.g., λgt10 and EMBL3. The resulting ligation mixture is used to transform an appropriate host, e.g., the strain LE392 or WL95 of *Escherichia coli*, to give a human genomic library. Positive clones were obtained by synthetic probes. The desired phage DNA is recovered from one of the clones, digested with an appropriate restriction enzyme, e.g., BamHI or HindIII, and introduced into an appropriate plasmid vector, e.g., pUC19. The desired clone can be obtained through transformation of a host, e.g., *Escherichia coli* JM109.

As plasmids having the nucleotide base sequence containing the promoter region of the present invention incorporated therein, there may be mentioned pCG1, pCG11 and pCG111 (see the accompanying drawings for the restriction enzyme maps).

The nucleotide base sequence of the DNA in question can be determined by a known method, e.g., the kilobase sequencing method, Maxam-Gilbert method or dideoxy method.

The promoter region according to the invention is present upstream from the 5' end of the transcription initiation site for the CSF-1 gene. It is at least about 520 bp long. The nucleotide base sequence of the CSF-1gene promoter-containing region, as determined by the kilobase sequencing method, is in FIGS. 1A and 1B.

In this promoter region, a TATA box has not yet been identified. The but TATA box is considered to be in the $-51$ to $-46$ region having the nucleotide base sequence of CATAAA in the $-23$ to $-18$ region having the nucleotide base sequence of TTAAAA. The promoter region also includes a G−T cluster region ($-124$ to $-77$) (Rich, et al., Ann. Rev. Biochem., 53, 792-846 (1984)), a region homologous to the enhancer-core region of the immunoglobulin heavy chain gene ($-131$ to $-123$) (Khoury et al., Cell, 33, 313-314 (1983)) and a region homologous to the consensus region upstream from the lymphokine gene ($-520$ to $-511$, $-448$ to $-439$ and $-60$ to $-51$) (Stanley, et al., EMBO Journal, 4, 2569-2573 (1985)).

The human CSF-1 gene promoter region according to the invention has a novel nucleotide base sequence and can be utilized as a vector for expression in animal cells when at least the DNA sequence thereof between the PstI ($-556$) and SmaI ($+15$) sites is used as a promoter and the DNA sequence of a desired gene to be expressed is joined thereto.

In order to produce the desired product, the host animal cells are transfected with the expression vector containing the promoter of the present invention and the desired product gene joined adjacent thereto.

Examples of the desired product gene which can be expressed using the promoter of the present invention include the genes coding for urokinase, hepatitis B antigen, human serum albumin, interferon-α, interferon-B, interferon-γ and derivatives thereof.

Preferable examples of host animal cells to be used in the present invention include mouse L cell, human T cell-derived cell line such as CCRM-CEM and human tumor cell-derived cell line such as MIA-PaCa.

The following example illustrates the present invention in further detail, but is no way intended to limit the scope of the present invention.

EXAMPLE (1) Preparation of chromosomal DNA (a) Extraction of human liver DNA

Human liver (10 g) stored frozen at $-80°$ C. was minced finely and then homogenized in 50 ml of 10 mM Tris-hydrochloride buffer (pH 8.0) containing 100 μg/ml protease K (Merck), 0.5% (w/v) Sarkosyl (Wako Pure Chemical Industries) and 0.5 M EDTA. After incubation at 50° C. for 3 hours, the homogenate was extracted with distilled phenol saturated with 10 mM Tris-hydrochloride buffer (pH 8.0) containing 1.0 mM EDTA (hereinafter "TE buffer"). The aqueous layer thus obtained was dialyzed overnight against 50 mM Tris-hydrochloride buffer (pH 8.0) containing 10 mM sodium chloride and 10 mM EDTA.

This DNA solution was treated with 100 μg/ml RNase A (Sigma) at 37° C. for 3 hours (as described in Maniatis et al., supra) and then extracted with phenol-chloroform (1:1). The aqueous layer was recovered and dialyzed overnight against TE buffer. Thus was obtained 11.7 mg of purified human liver DNA.

(b) Partial digestion with a restriction enzyme

A 1.27 mg portion of the human liver DNA was dissolved in 7.5 ml of 10 mM Tris-hydrochloride buffer (pH 7.5) containing 7 mM MgCl$_2$ and 0.1 M NaCl and treated with a restriciton enzyme (Sau3AI, 5.0 units) at 37° C. for 30 minutes, whereby a partial digest was obtained.

(c) Sucrose density gradient centrifugation

After phenol-chloroform (1:1) extraction, the partially digested DNA was precipitated with ethanol and the precipitate was dissolved in 0.5 ml of TE buffer. After heating at 65° C. for 3 minutes and subsequent cooling, the sample was fractionated by centrifugation (26,000 rpm, 20° C., 24 hours) on a 10–40% (w/v) sucrose density gradient and a DNA fragment fraction of approximately 20 kbp was recovered. Molecular weight analysis was performed by 0.5% (w/v) agarose gel electrophoresis using pBR322 linear oligomers as molecular weight markers (Maniatis, et al., supra).

The recovered fraciton was dialyzed against TE buffer. 2-Butanol extraction and ether extraction were carried out and further ethanol precipitation was conducted to give 74 μg of purified DNA fragment.

(2) Production of a gene library (a) EMBL3 (Amersham) was used as the ligation vector for the partially digested human liver DNA. EMBL3 arm (500 ng) and the partially digested human liver DNA (170 ng) were dissolved in 5 μl of 66 mM Tris-hydrochloride buffer (pH 7.6) for T4 DNA ligase treatment containing 6.6 mM MgCl$_2$, 10 mM dithiothreitol, 0.1 mM ATP and the ligation reaction was carried out in the presence of 300–400 U of T4 DNA ligase (Takara Shuzo) at 16° C. overnight.

(b) In vitro packaging

In vitro packaging was performed using the Gigapack TM kit (Vector Cloning System). The titer of the phage solution obtained by packaging of the ligation mixture obtained as described above under (a) was $3.6 \times 10^6$ pfu (plaque forming units)/ml as determined by using *Escherichia coli* WL95 (Amersham) as an indicator organism.

(3) Screening (a) Probe designing and DNA synthesis

For screening, probes were designed based on the cDNA sequence for CSF-1 as reported by Kawasaki et al. (Science, 230, 291–296 (1985)). Two probes were synthesized, a 24mer DNA sequence corresponding to the 3rd to 10th amino acids (probe 1, GTG TCG GAG TAC TGT AGC CAC ATG) and a 63mer DNA sequence corresponding to the 23rd to 43rd amino acids (probe 2, ATT GAC AGT CAG ATG GAG ACC TCG TGC CAA ATT ACA TTT GAG TTT GTA GAC CAG GAA CAG TTG).

(b) Terminal labeling of the probe DNAs

The probe DNAs were terminally labeled using [γ-$^{32}$P]ATP (Amersham) and T4 polynucleotide kinase (Takara Shuzo). The reaction was carried out in 30 μl of reaction mixture containing 70 mM Tris-hydrochloride (pH 7.6), 10 mM MgCl$_2$ and 5 mM DTT in the presence of 6 units of T4 DNA kinase at an ATP:5'-OH mole ratio of 1:3. As a result, probes having a specific radioactivity of $2 \times 10^7$ to $1 \times 10^8$ cpm (Cerenkov Counting)/μg DNA were obtained.

(c) Screening of the genomic library (i) For screening of about $1.5 \times 10^6$ pfu of the above genomic library, 30 plates (Falcon No. 1058 15-cm plates) were inoculated with $5 \times 10^4$ pfu of phage per plate. *Escherichia coli* WL95 was used as an indicator for the phage. The agar medium used was TB10 medium comprising 10 g/liter Bacto-tryptone, 5 g/liter NaCl, 10 mM MgSO$_4$.7H$_2$O, and 1.5% (w/v) Bacto Agar. Plaques were transferred to nitrocellulose filters (S&S) according to the method of Maniatis, et al., supra and subjected to alkali denaturation and fixation. For prehybridization, incubation was carried out at 42° C. for 3 hours in a solution containing 6×SSC (1×SSC=0.15 M NaCl, 0.015 M sodium citrate), 5×Denhardt's solution (Maniatis et al., supra), 50 mM sodium phosphate, pH 6.8, 0.1% (w/v) SDS (sodium dodecyl sulfate), 10% (w/v) dextran sulfate and 100 μg/ml sonicated salmon sperm DNA (heated at 90° C. and then cooled). Hybridization was effected by incubating overnight at 37° C. in the same solution with the 63mer probe added in a concentration of about $5.0 \times 10^5$ cpm/ml. Filter washing was conducted at a temperature of 55° C. using a solution containing 6×SSC and 0.1% (w/v) SDS. As a result, about 30 spots each showing a strong signal were obtained.

(ii) Secondary screening

The 30 spots obtained by the primary screening and showing a strong signal were subjected to secondary screening using the 24mer and the 63mer probes as described above. Since the plaque density was about the primary screening was about 200 plaques/cm$^2$, 9-cm dishes (Falcon, No. 1029) were used for the secondary screening so that a plaque density of about 3 plaques/cm$^2$ could be obtained. The filter washing temperature was 55° C. for those filters for which the 63mer probe had been used. The filter washing temperature was 45° C. for those filters for which the 24mer probe had been used. Of the 30 spots showing a strong signal in the primary screening, 10 spots gave strong signals with both the probes.

(iii) Tertiary screening

Two to six single plaques were isolated from each plate showing a strong signal in the secondary screening, and DNA purification was carried out by the simplified extraction method (Benson, et al., Biotechniques, 2, 126–127 (1984)). The DNA from each clone was digested with BamHI and HindIII, and the resulting DNA fragments were separated for pattern comparison by agarose gel electrophoresis. According to the report of Kawasaki et al., supra, BamHI digestion of the CSF-1 gene gives a fragment of about 2.8 kb and HindIII digestion thereof gives a fragment of about 4.0 kb. Therefore, the results obatined were analyzed using these two fragments as indicators. As a result, a clone having both fragments (about 4.0 kb HindIII fragment and about 2.8 kb BamHI fragment) and a clone having the about 2.8 kb BamHI fragment alone were found. The clone having both the fragments was named clone 1 and the clone having the BamHI fragment alone was named clone 2.

(d) Properties of clone 1

For investigating the properties of the thus-obtained phage clone 1, phage DNA was prepared by the method of Maniatis et al., supra and the restriction enzyme digestion patterns were studied. The results are shown in the Table below.

Table

| Restriction enzyme | DNA fragment size (kbp) | | |
| --- | --- | --- | --- |
| SalI | 16.5 | — | — |
| HindIII/SalI | 10.5 | 4.2 | 1.6 |
| HindIII | 30 | 6.4 | 4.2 |
| BamHI | 12 | 2.8 | 1.7 |
| BamHI/SalI | 12 | 2.8 | 1.7 |

It was thus revealed that a chromosomal DNA fragment of about 16.5 kb had been cloned in clone 1.

(4) Subcloning

Clone 1 was digested with HindIII or BamHI and the chromosomal DNA was subcloned in the plasmid pUC19 (Pharmacia). *Escherichia coli* JM109 (Takara Shuzo) was used as the host and was transformed by the RbCl method (Hanahan, DNA Cloning, vol. 1 (1985), edited by Glover, IRL Press). The plasmid DNA was isolated from the transformants and the restriction enzyme map of the plasmid DNA was prepared. Screening of the transformants obtained gave 5 subclones, from among which the desired plasmid pCG1 was obtained. In pCG1, there is cloned a fragment of about 12 kb resulting from BamHI digestion of phage clone 1, in the plasmid pUC19 at the BamHI site thereof (FIG. 2).

Figure 5:
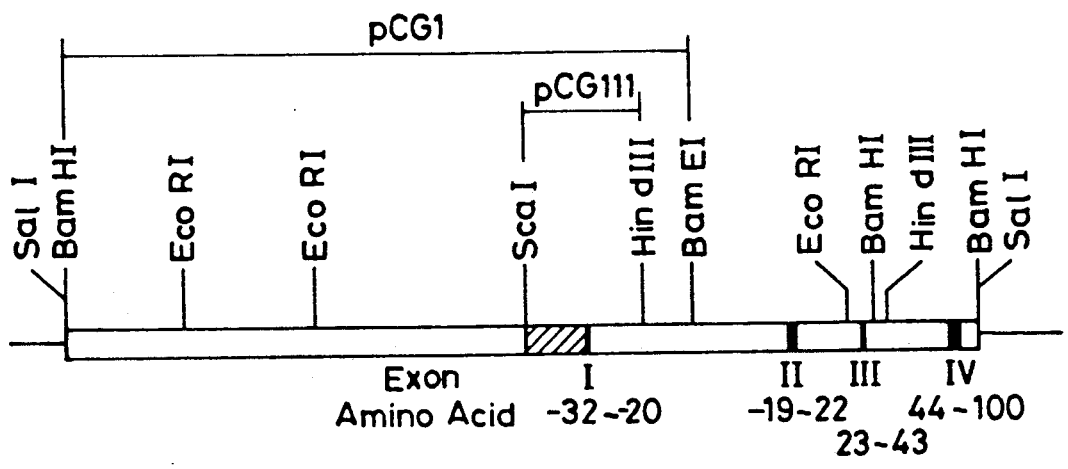
FIG. 5 shows the structure of the CSF-1 gene on clone 1.

As described in detail below, analysis of this plasmid revealed that an intron exists between the codon for amino acid −10 and the codon for amino acid −19 within the signal peptide and that Exon I comprising the codons for amino acid −32 to amino acid −20 occurs in the DNA pCG1 (FIG. 5).

(5) Analysis (a) Construction of a restriction enzyme map of pCG1

A restriction enzyme map of the BamHI fragment of the CSF-1 gene as cloned in pCG1 was constructed.

Figure 3:
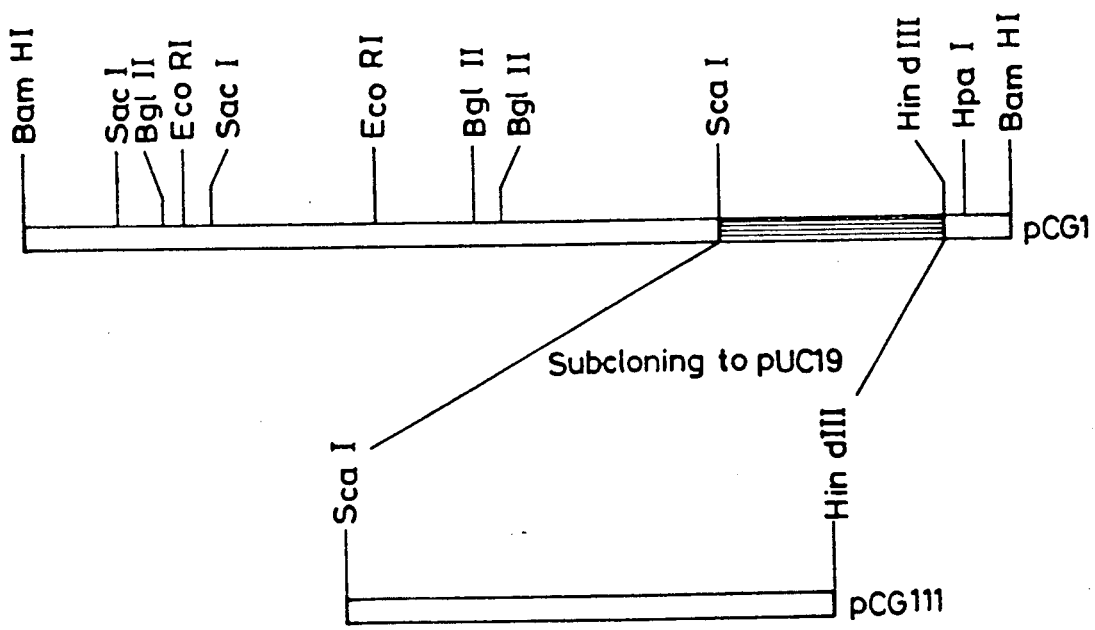
FIG. 3 shows the restriction enzyme map of pCG1 as well as the subcloning thereof.

Since the BamHI fragment subcloned in pCG1 was as large in size as about 12 kb, restriction enzyme map construction was difficult to realize. Therefore, as shown in FIG. 2, said fragment was divided into four fragments by making use of the EcoRI and HindIII sites and the respective fragments were subcloned in pUC19 to give pCG11 to pCG14. For mapping pCG11 to pCG14 as well as pCG1, digestion was performed with various restriction enzymes and, as a result, the restriction enzyme map shown in FIG. 3 was obtained.

(b) Mapping of Exon I by Southern analysis

Based on the restriction enzyme map of pCG1 (FIG. 3), mapping of Exon I was carried out by the southern hybridization method (Maniatis, et al., supra). The probe used was a sequence in the neighborhood of the 5' end of the CSF-1 cDNA, namely 5'-GCCGGCTCTCTGGCGCCGAGAGG-3'. The results of mapping of Exon I by Southrn analysis revealed that Exon I occurs in the ScaI-HindIII fragment (about 2.6 kb) of pCG1. Therefore, this ScaI-HindIII fragment was subcloned in pUC19 at the HincII-HindIII site thereof and the thus-constructed plasmid pCG111 (FIG. 3) was used for DNA sequence determination.

(c) Preparation of deletion DNAs

For carrying out kilobase sequencing, deletion DNAs were prepared using the deletion kit (Takara Shuzo), which contains exonuclease III (which cleaves only 5'-protruding DNAs), mung bean nuclease (which cleaves only single-stranded DNAs) and T4 DNA polymerase and ligase kit. For preparing one-way deletion DNAs from the ScaI site side of the CSF-1 gene fragment subcloned in pCG111, ScaI was allowed to act on the restriction enzyme site on the non-deletion side (3'-protruding) and exonuclease III was allowed to act on the restriction enzyme site (rendering a BamHI site) on the deletion side.

According to the kit instruction, deletion (hereinafter, Δ) DNAs varing in size were obtained from pCG111. ΔDNAs were selected at intervals of about 200-300 bases and used in base sequence determination.

(d) DNA base sequence determination

Figure 4:
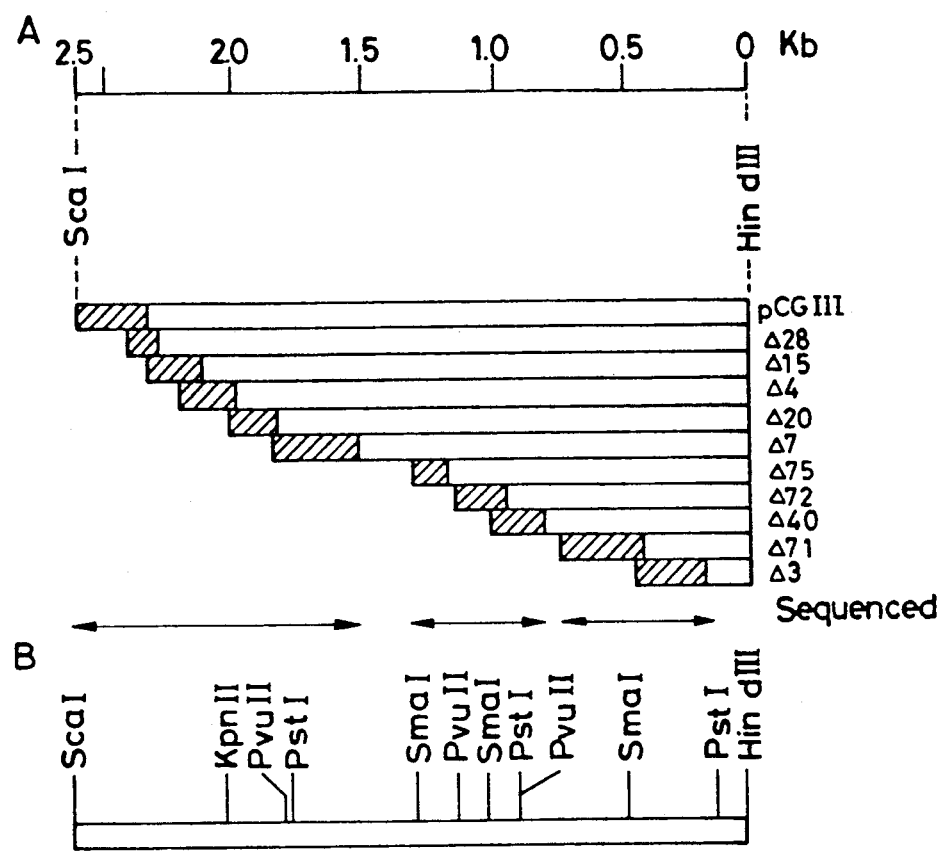
FIG. 4 shows the nucleotide base sequence determination region of each deletion clone.

The base sequence of each Δ clone DNA obtained as described in the preceding section was determined using the M13 sequencing kit (Takara Shuzo). The base sequence determination region of each clone is shown in FIG. 4.

The kilobase sequencing method employed failed to determine the boundary regions of the Δ7 clone and Δ75 clone (about 200 bases) and of the Δ40 and Δ71 clones (about 80 bases). Therefore, the sequences of these regions were determined by using, as a primer, the DNA probe used in mapping Exon I by Southern analysis. As a result, the nucleotide base sequence of about 1,300 base pairs upstream from Exon I as occurring in the ScaI-HindIII fragment contained in pCG111 was determined.

Figure 6:
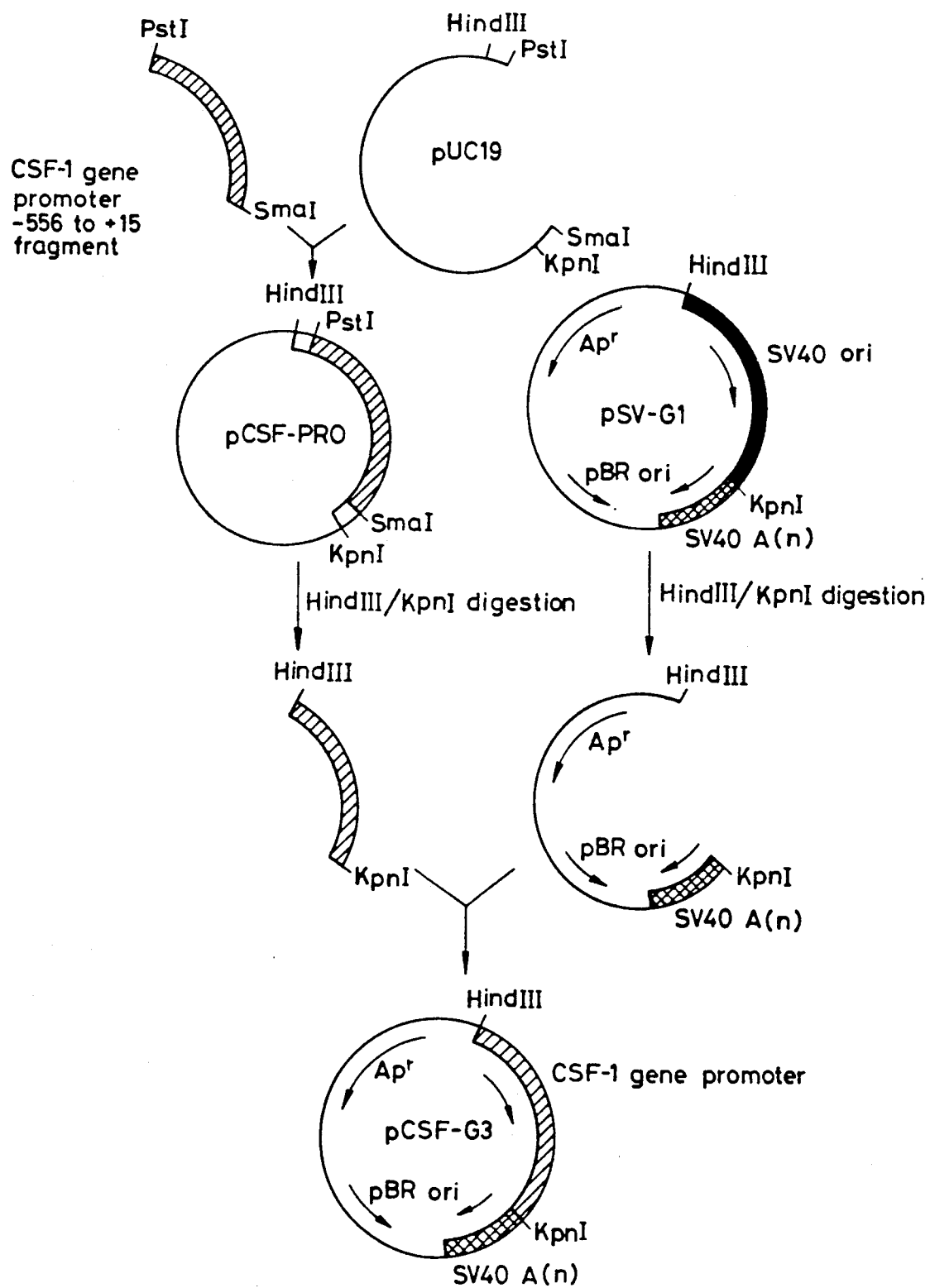
FIG. 6 shows a scheme of construction of pCSF-G3.

(6) Expression in animal cells (a) Construction of expression vector pCG111 was digested with PstI and SmaI and the PstI-SmaI fragment (about 570 bp) was isolated by 1% agarose gel electrophoresis (as described in Maniatis, et al., supra). This fragment was inserted into PstI-SmaI site of pUC19 to obtain the plasmid pCSF-PRO. Then, pCSF-PRO was digested with HindIII and KpnI to obtain the CSF-1gene promoter region as a HindIII-KpnI fragment. Separately, the plasmid pSV-G1 used for expression in animal cells (EP154272A) was digested with HindIII and KpnI and the above HindIII-KpnI fragment was inserted thereto to obtain the plasmid pCSF-G3 (FIG. 6). The CSF-1gene promoter-containing expression vector was prepared by inserting the desired product gene into unique restriction enzyme KpnI site of pCSF-G3.

(b) Construction of urokinase gene-containing expression vector

Figure 7:
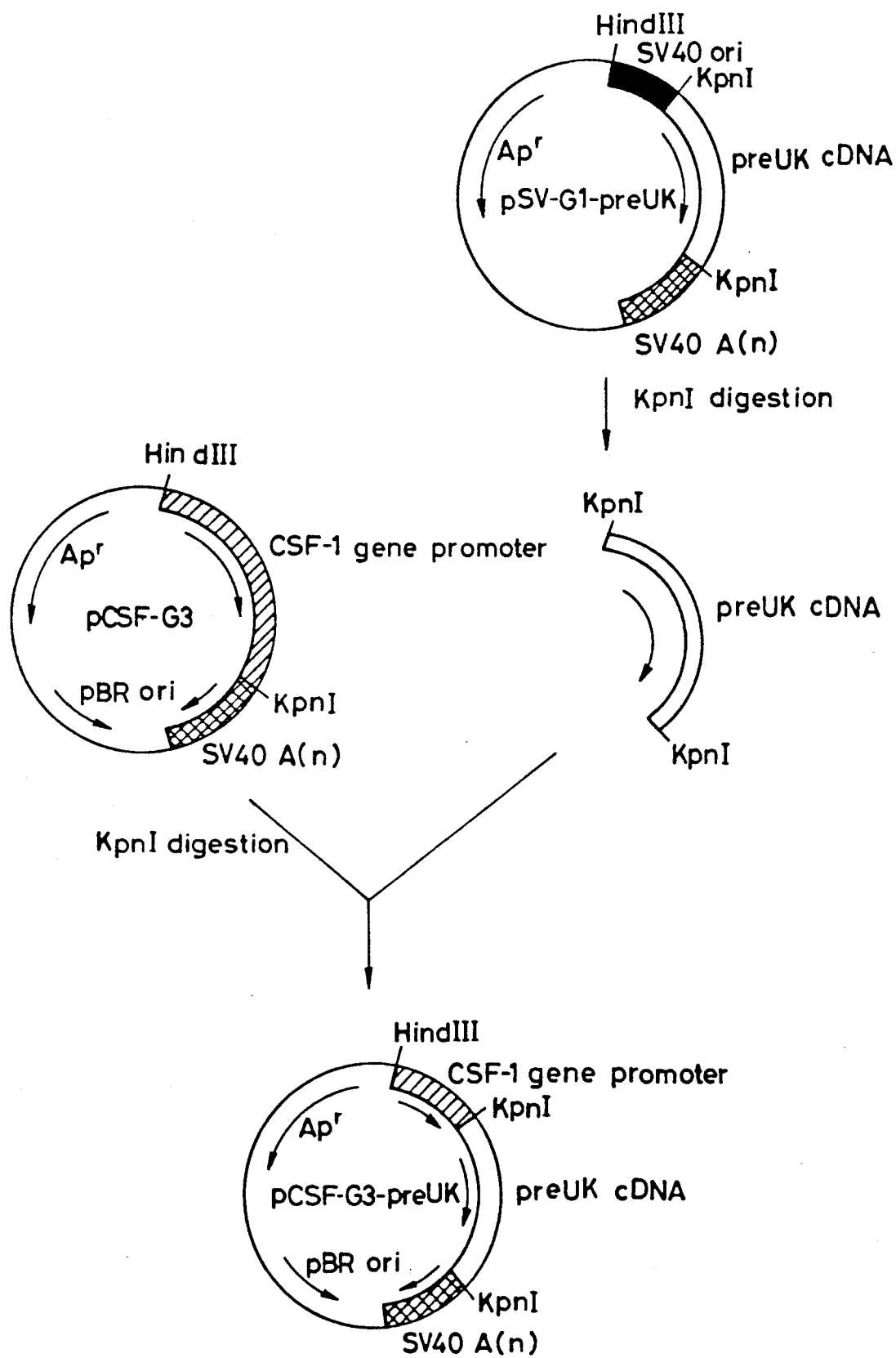
FIG. 7 shows a scheme of construction of pCSF-G3-preUK.

The urokinase cDNA-containing plasmid, pSV-G1-preUK (EP154272A) was digested with KpnI and the DNA fragment containing preUK cDNA was isolated by agarose gel electrophoresis. The DNA fragment obtained was inserted into KpnI site of pCSF-G3 to obtain the pCSF-G3-preUK (FIG. 7).

(c) Transfection of animal cells pCSF-G3-preUK and pSV-G1-NEO (EP154272A) was mixed in a molar ratio of 1,000:1 and the mixture was used to transfect CCRM-CEM-derived cell line by electroporation (Potter, et al., Proc. Natl. Acd. Sci. USA, 81, 7161-7165 (1984)). Thus, the transformants resistant to G418were obtained and it was found that about 25% of the transformants allowed urokinase production.

While the invention has been described in detail and with reference to specific embodiments thereof, it will be apparent to one skilled in the art that various changes and modifications can be made therein without departing from the spirit and scope thereof.

What is claimed is:

1. A CSF-1 expression vector comprising nucleotides −1 to −520 of FIG. 1A and FIG. 1B and operably linked to a heterologous gene wherein the expression of said heterologous gene is controlled by the CSF-1 nucleotide sequence.

2. The expression vector of claim 1, wherein said heterologous gene is selected from the group consisting of the genes coding for urokinase, hepatitis B antigen, albumin and interferon.

3. A mammalian cell transformed with the expression vector of claim 1.

4. The mammalian cell of claim 3, wherein said cell is selected from the group consisting of mouse L cells, a human T cell-derived cell line and a human tumor cell-derived cell line.

* * * * *